(12) United States Patent
Kanitz

(10) Patent No.: US 8,481,785 B2
(45) Date of Patent: Jul. 9, 2013

(54) MATERIALS FOR N-DOPING THE ELECTRON-TRANSPORTING LAYERS IN ORGANIC ELECTRONIC COMPONENTS

(75) Inventor: Andreas Kanitz, Hoechstadt (DE)

(73) Assignee: Osram Opto Semiconductors GmbH, Regensburg (DE)

( * ) Notice: Subject to any disclaimer, the term of this patent is extended or adjusted under 35 U.S.C. 154(b) by 229 days.

(21) Appl. No.: 12/065,862

(22) PCT Filed: Aug. 23, 2006

(86) PCT No.: PCT/EP2006/065580
§ 371 (c)(1),
(2), (4) Date: Jul. 31, 2008

(87) PCT Pub. No.: WO2007/028712
PCT Pub. Date: Mar. 15, 2007

(65) Prior Publication Data
US 2009/0114906 A1 May 7, 2009

(30) Foreign Application Priority Data

Sep. 5, 2005 (DE) .......................... 10 2005 042 103

(51) Int. Cl.
*H01L 51/00* (2006.01)
*C07F 5/02* (2006.01)
*C07D 417/02* (2006.01)

(52) U.S. Cl.
USPC ............ 564/8; 544/14; 544/31; 568/3; 568/6; 428/690

(58) Field of Classification Search
USPC ....................................... 428/690
See application file for complete search history.

(56) References Cited

U.S. PATENT DOCUMENTS

2003/0152800 A1 * 8/2003 Tamao et al. ................. 428/690

FOREIGN PATENT DOCUMENTS

| EP | 0 775 706 A2 | 5/1997 |
| EP | 1 142 895 A1 | 10/2001 |
| WO | WO 00/40586 | 7/2000 |
| WO | WO 2005/062675 A1 | 7/2005 |

OTHER PUBLICATIONS

Negishi, "Pd-Catalyzed Amination of Aryl Halides and Related Reactions," *Handbook of Organopalladium Chemistry for Organic Synthesis: vol. 1* (John Wiley & Sons, Inc., New York, 2002), pp. 1061, 1091-1096.
"4-amino-2-methyl-naphthaline, 3-methyl-naphthylamine-(1)", Beilstein Handbook, vol. 12, No. II, pp. 743-744. (Translation included), 2008.
John F. Blount, "Conformational Analysis of Triarylboranes", Oct. 17, 1973, Journal of the American Chemical Society, vol. 95, No. 21, pp. 7019-7029.
Shighiro Yamaguchi et al., Tri-9-anthrylborane and Its Derivatives: New Boron-Containing π-Conjugation through Boron, 2000, Journal of the American Chemical Society, 122, pp. 6335-6336.
International Preliminary Report of Patentability and Written Opinion of the International Searching Authority, International Application No. PCT/EP2006/065580, Apr. 8, 2008, 8 pp.

* cited by examiner

*Primary Examiner* — Gerard Higgins
*Assistant Examiner* — J. L. Yang
(74) *Attorney, Agent, or Firm* — Fish & Richardson P.C.

(57) ABSTRACT

The invention pertains to new materials based on sterically inhibited donor arylboranes for the improvement of electron injection and electron transport in organic electronic components like organic light-emitting diodes (OLED's), organic field effect transistors (OFET's), and on organic photovoltaics based components, in particular, organic solar cells.

6 Claims, No Drawings

MATERIALS FOR N-DOPING THE ELECTRON-TRANSPORTING LAYERS IN ORGANIC ELECTRONIC COMPONENTS

BACKGROUND

The invention pertains to new materials for the improvement of the electron injection and the electron transport in organic components like organic light-emitting diodes (OLED's), organic field effect transistors (OFET's), and organic solar cells.

In recent years materials, in particular for organic light-emitting diodes, have become known, which improve electron injection and electron transport in OLED's. (Lit.: S. Yamaguchi, S. Akiyama, K. Tamao, J. Am. Chem. Soc. 2000, 122 6335-6336).

This also results in a lower operating voltage without affecting the efficiency of the OLED. These materials are strong electron donors, which are doped in small quantities into the electron transport layer or the emitter layer of the OLED. Such additions facilitate the reduction of the electron transport material or emitter material (i.e. acceptance of electrons into the LUMO [lowest unoccupied molecular orbital] of the electron or emitter material), which otherwise takes place due to the energy of the electric field only. As a result, a weaker electric field (i.e. a lower operating voltage) achieves the same efficiency.

In the currently known materials, the stability and the injection as well as the electron-facilitating effect are not satisfactory yet.

SUMMARY

It is therefore the objective of this invention to create a material for improved electron injection and/or electron transport in organic components, which overcomes the shortcomings of the state of the art, and increases in particular the current lack of stability of the injection and electron transport-facilitating effect.

The solution to this problem and object of the invention is disclosed in the claims, the embodiments and the description.

DETAILED DESCRIPTION

According to the invention, the injection and electron transport-facilitating effects can further be increased by the new sterically hindered donor arylboranes of substructures 1 and 2. The materials are also stable when exposed to air, not susceptible to hydrolysis, and sublimable.

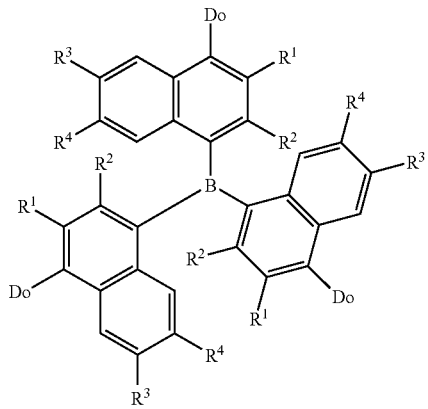

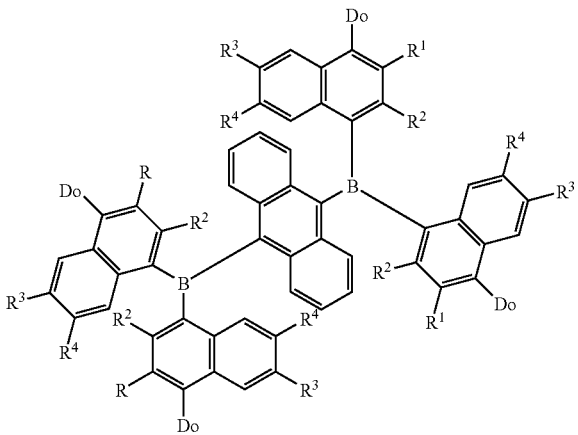

The following applies:

Do is an electron donor, most suitably nitrogen, which is substituted by aromatics (phenyl or naphthyl).

$R^1$ und $R^2$ either form another annelated aromatic ring or $R^1$ forms a bridge to a donor substituent, most suitably sulfur, $R^2$ is in this case H or methyl.

$R^3$ and $R^4$ may be hydrogen or jointly form an annelated aromatic ring.

Typical electron donors are aromatic systems and any electron-rich systems like thiophenes, alkyl-substituted or sulfur-carrying, multinuclear aromatic systems, and any low electron-negative substituents, preferably electron-rich low electron-negative substituents.

The new materials capable of improving electron transport and electron injection by way of chemical interaction with any electron transporting and/or emitter layers can therefore successfully be used in any polymer-electronic components, including any technologies for the manufacture of organic light-emitting diodes (OLED's), organic field effect transistors (OFET's), and organic solar cells.

Embodiments 1)
a) Synthesis of 9-diphenylamino-anthracene through coupling of diphenylamine and 9-bromoanthracene by a Heck reaction.
b) Synthesis of 10,10,10-tris-9-diphenylamino-anthryl-boran from 9-diphenylamino-anthracene, BuLi and borontribromide at −70° C.

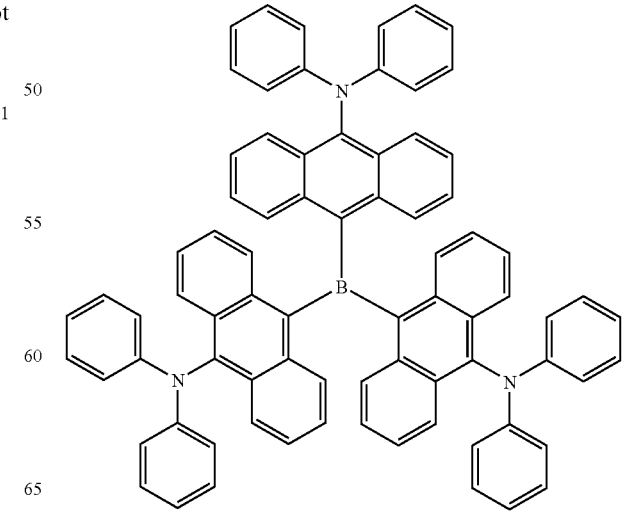

2)
a) Synthesis of 3-methyl-1-naphthylamine per Beilstein manual 12,II,744.
b) Synthesis of 1-diphenylamino-3-methyl-naphthaline through coupling from 3-methyl-1-naphthylamine and bromobenzene by a Heck reaction.
c) Synthesis of benzo-f-6-methyl-10-phenyl-phenothiazine from 1-diphenylamino-3-methyl-naphthaline and sulfur.
d) Synthesis of 7,7,7-tris-benzo-f-6-methyl-10-phenyl-phenothiazinyl-borane from benzo-f-6-methyl-10-phenyl-phenothiazine, BuLi and borontribromide at −70° C.

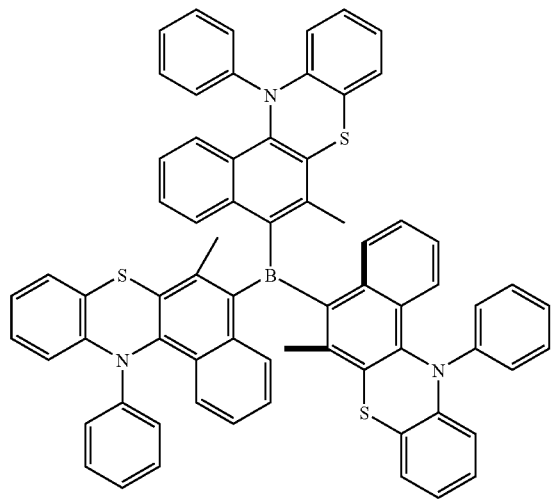

3)
a) Synthesis of 9-diphenylamino-anthracene through coupling of diphenylamine and 9-bromoanthracene by a Heck reaction.
b) Synthesis of tetra-(9-diphenylamino-anthr-10-yl)-9,10-anthrylendiborane from 9,10-dibromoanthracene, 9-diphenylamino-anthracene, BuLi and borotribromide at −70° C.

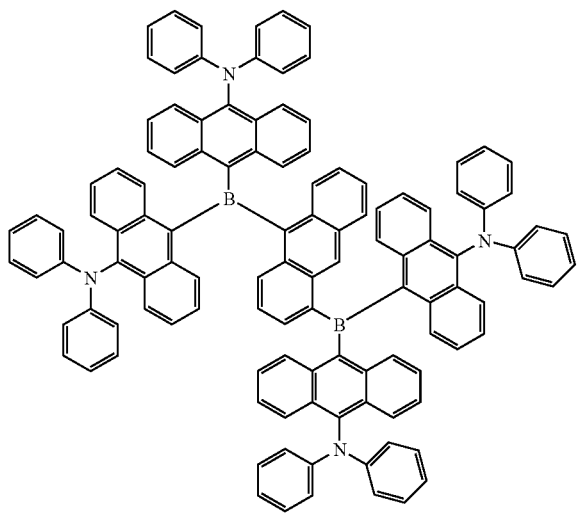 [SMILES: c1ccc(N(c2ccccc2)c2c3ccccc3c(B(c3cccc4c(B(c5c6ccccc6c(N(c6ccccc6)c6ccccc6)c6ccccc56)c5c6ccccc6c(N(c6ccccc6)c6ccccc6)c6ccccc56)c5ccccc5cc34)c3c4ccccc4c(N(c4ccccc4)c4ccccc4)c4ccccc34)c3ccccc23)cc1]

The invention pertains to new materials based on sterically inhibited donor arylboranes for the improvement of electron injection and electron transport in organic electronic components like organic light-emitting diodes (OLED's), organic field effect transistors (OFET's), and organic photovoltaic components, in particular solar cells.

The invention claimed is:
1. Material for n-doping of an electron-transporting layer in organic electronic components, wherein said material comprises at least one sterically inhibited donor arylboranes of substructures 1 and 2,

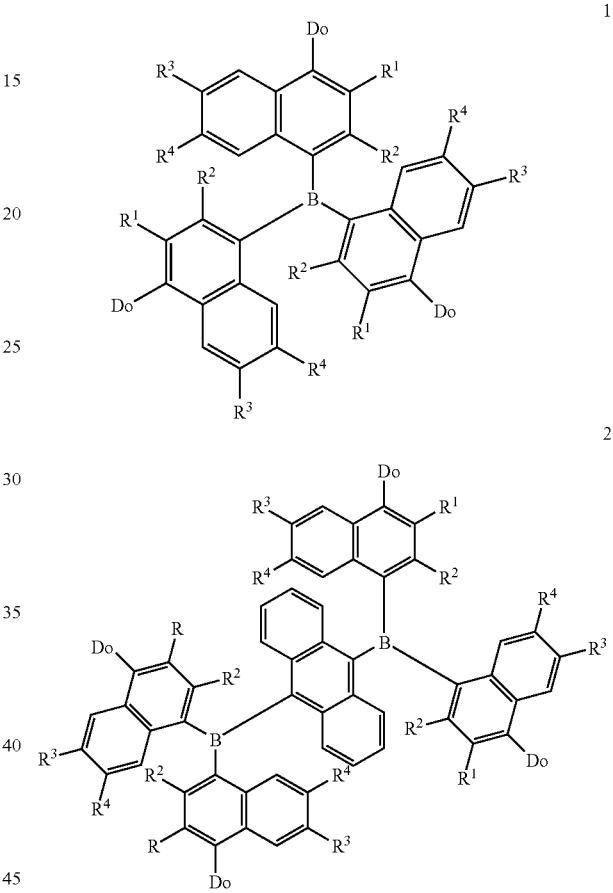

wherein:
Do represents an electron donor,
$R^1$ is sulfur and forms a bridge to the neighboring donor substituent Do,
$R^2$ is H or methyl, and
$R^3$ and $R^4$ can be hydrogen or form a joint annelated aromatic ring.

2. Material according to claim 1 with Do in one of substructures 1 or 2 selected from a group of functional groups comprising nitrogen with an aromatic substituent.

3. Method for n-doping an electron-transporting layer of an organic electronic component, the method comprising n-doping the electron-transporting layer with a material according to claim 1.

4. Organic electronic component comprised of at least two electrodes with an active layer, wherein located between at least one electrode and the active layer is an electron-transporting layer doped with a material according to claim 1.

5. Material according to claim 1, comprising the following sterically inhibited donor arylborane structure:

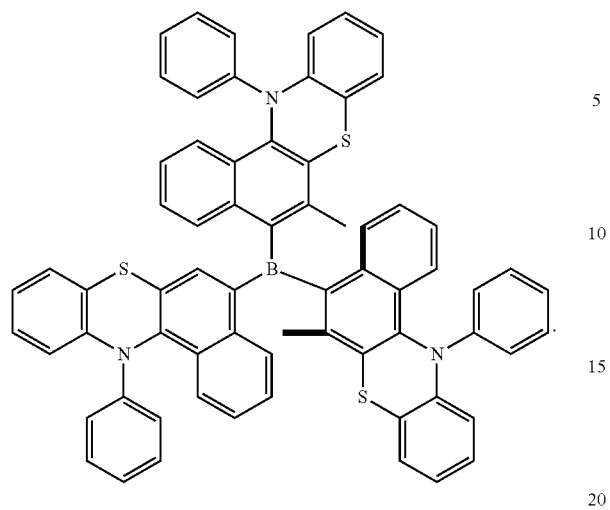
6. Material according to claim 1 with Do in one of substructures 1 or 2 selected from a group of functional groups comprising nitrogen with a phenyl or naphthyl substituent.
* * * * *

UNITED STATES PATENT AND TRADEMARK OFFICE
CERTIFICATE OF CORRECTION

PATENT NO.        : 8,481,785 B2
APPLICATION NO.   : 12/065862
DATED             : July 9, 2013
INVENTOR(S)       : Andreas Kanitz Page 1 of 1

It is certified that error appears in the above-identified patent and that said Letters Patent is hereby corrected as shown below:

In the Claims
Column 5
Claim 5, lines 1-20 (approx.), delete "
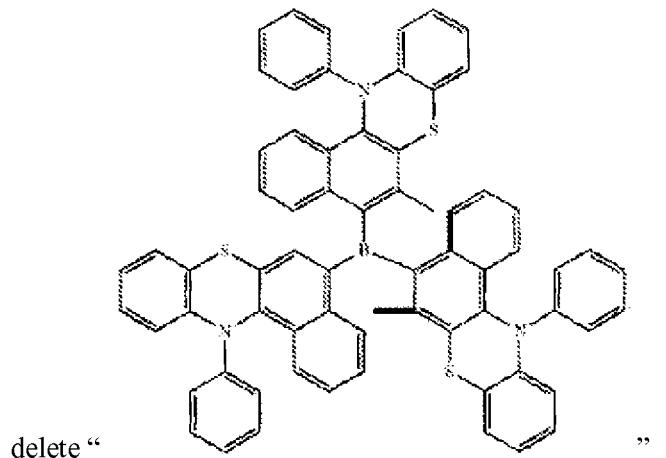
"

and insert --
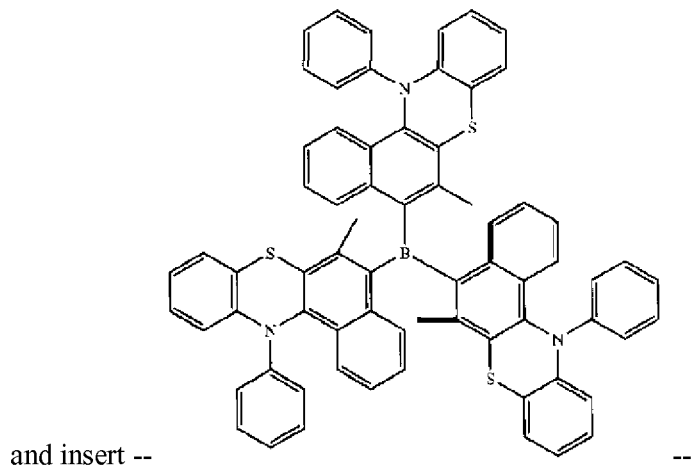
--

Signed and Sealed this
First Day of October, 2013

Teresa Stanek Rea
*Deputy Director of the United States Patent and Trademark Office*